(12) United States Patent
Kim et al.

(10) Patent No.: US 10,017,779 B2
(45) Date of Patent: Jul. 10, 2018

(54) GENE IMPLICATED IN ABIOTIC STRESS TOLERANCE AND GROWTH ACCELERATING AND USE THEREOF

(71) Applicant: INDUSTRY-ACADEMIC COOPERATION FOUNDATION, YONSEI UNIVERSITY, Seoul (KR)

(72) Inventors: Woo Taek Kim, Goyang-si (KR); Eun Yu Kim, Seoul (KR); Ji Ho Seo, Seoul (KR); Ki Youl Park, Seoul (KR)

(73) Assignee: INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 48 days.

(21) Appl. No.: 15/178,905

(22) Filed: Jun. 10, 2016

(65) Prior Publication Data

US 2017/0022513 A1  Jan. 26, 2017

Related U.S. Application Data

(63) Continuation of application No. 13/964,071, filed on Aug. 10, 2013, now Pat. No. 9,534,231.

(30) Foreign Application Priority Data

Aug. 10, 2012 (KR) .......................... 10-2012-0087959

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/825* (2013.01); *C12N 15/8251* (2013.01); *C12N 15/8261* (2013.01)

(58) Field of Classification Search
None
See application file for complete search history.

(56) References Cited

U.S. PATENT DOCUMENTS

| | | | |
|---|---|---|---|
| 7,214,786 B2 | 5/2007 | Kovalic et al. | 536/23.6 |
| 7,612,177 B2 | 11/2009 | Salort et al. | 530/370 |
| 8,228,661 B2 | 7/2012 | Ito et al. | 361/301.4 |
| 2006/0235215 A1 | 10/2006 | Cooper | 536/23.6 |
| 2009/0260109 A1 | 10/2009 | Ronen et al. | 800/290 |
| 2010/0319088 A1 | 12/2010 | Ronen et al. | 800/289 |
| 2011/0247101 A1* | 10/2011 | Alexandrov | C07K 14/415 |
| | | | 800/298 |

FOREIGN PATENT DOCUMENTS

WO  WO 2011/108795  9/2011  ............... A01H 5/00

OTHER PUBLICATIONS

Kim et al, 2016, Plant Phys., 170:2494-2510.*
Chen, L., et al. (2011) "Identification and survey of pre-mRNA splicingrelated proteins in 10 plant species." Graduate Theses and Dissertations, *Iowa State University Digital Repository @ Iowa State University*.
Liu, H., et al. (2008) "Functional analysis reveals pleiotropic effects of rice RING-H2 finger protein gene OsBIRF1 on regulation of growth and defense responses against abiotic and biotic stresses." *Plant Mol. Biol.* 68:17-30.
Wititsuwannakul, R., et al. (2008) "A rubber particle protein specific for Hevea latex lectin binding involved in latex coagulation." *Phytochemistry*, 69:1111-1118.

* cited by examiner

*Primary Examiner* — Jason Deveau Rosen
(74) *Attorney, Agent, or Firm* — Harness, Dickey & Pierce, P.L.C.

(57) ABSTRACT

The present invention provides a method for improving the tolerance of a plant to an abiotic stress and a method for promoting growing of a plant, comprising a nucleotide sequence encoding the AtSRP (*Arabidopsis thaliana* stress related protein) of a plant. The present nucleotide sequence is involved in abiotic stress tolerance such as drought, low-temperature and salt stresses of plants. Therefore, the overexpressing transgenic plants have excellent tolerances to these abiotic stresses, whereby they may be useful as novel functional crops which are affected by climates and environments of the cultivated areas. In addition, where the plants are transformed with the present nucleotide sequence, the growth abilities of the transgenic plants are remarkably enhanced, whereby they may effectively used for cultivating the plants with novel function of rapid growing, and biomass.

10 Claims, 14 Drawing Sheets

GENE IMPLICATED IN ABIOTIC STRESS TOLERANCE AND GROWTH ACCELERATING AND USE THEREOF

CROSS-REFERENCE TO RELATED APPLICATIONS

This application is a continuation application of U.S. application Ser. No. 13/964,071, filed on Aug. 10, 2013, Published as U.S. 2014/0143907 on 22 May 2014, which claims priority from Korean Patent Application No. 10-2012-0087959, filed on Aug. 10, 2012, in the Korean Intellectual Property Office, the entire disclosures of the applications identified in this paragraph of which are incorporated herein by references.

BACKGROUND OF THE INVENTION

Field of the Invention

The present invention relates to a gene implicated in abiotic stress tolerance and growth promotion and a method for improving abiotic stress tolerance and promoting growing of transformed plants with the same.

Description of the Related Art

Due to their sessile nature, higher plants are constantly faced with various adverse environmental factors, including drought, high salt, heavy metals, cold, heat shock, and ozone, during their whole life span. These abiotic stresses are a limiting factor for the growth and development of crop plants. Water deficiency causes dramatic reduction of crop production globally, and the decreasing availability of fresh water may pose a future threat to humans and higher plants. Plants have cellular and genetic defense mechanisms to enhance their tolerance to transient and long-term water shortages by triggering signaling network pathways and inducing stress-responsive genes (Shinozaki and Yamaguchi-Shinozaki, 2007). However, for stress tolerance or sensitivity, our knowledge concerning the biological functions of stress-related genes in higher plants is still rudimentary. Therefore, it is important to study the functions of stress responsive genes to increase the productivity of crop plants.

Plants have diverse defense strategies to reinforce their tolerance against unfavorable conditions by triggering signaling network pathways and inducing the stress-responsive genes. The present inventors have found that three AtSRP (*Arabidopsis thaliana* stress related protein) genes which encode homologs to the small rubber particle protein (SRPP) in rubber trees (*Hevea brasiliensis*) were rapidly induced by dehydration in *Arabidopsis thaliana*. Natural rubber is cis-1,4-polyisoprene produced through mevalonate pathway in cytosolic fractions (latex) of latex vessel tissues (Oh et al. 1999; Sookmark et al. 2002; Kim et al. 2004; Chow et al. 2007). Since *Arabidopsis thaliana* does not produce natural rubber, it was unexpected that the *Arabidopsis thaliana* water stress-induced genes shared sequence homology with rubber biosynthetic genes.

SRPP, originally known as a latex allergin, is a protein tightly bound on a small rubber particle in the latex of rubber trees (*Hevea brasiliensis*).

Bark tissue of rubber trees is constantly stripped, which is known as a tapping process, to collect rubber latex. Therefore, plugging of latex vessels is essential for rubber trees to prevent the loss of their cytoplasmic components, such as primary metabolites, and to prevent pathogen infection of the latex vessel tissues (Wititsuwannakul et al., 2008b). In the process of latex vessel plugging, hevein or *Hevea* latex lectin (HLL) interacts with rubber particle (RP) protein to form a rubber latex coagulum (Gidrol et al., 1994; Wititsuwannakul et al., 2008a). Recently, SRPP was purified as an RP glycoprotein that bound HLL and was, therefore, termed HLL-binding protein (HLLBP) (Wititsuwannakul et al., 2008c). Interaction between an N-acetylglucosamine moiety in SRPP and HLL may modulate the degree of latex coagulation in response to tapping and mechanical wounding.

However, roles of the SRPP associated with abiotic stresses such as drought, high salt and cold have been not known yet.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY OF THE INVENTION

The present inventors have made intensive studies to increase the productivity of crop plants by developing genes for improving a tolerance to abiotic stresses including drought, high salt and cold of the plants. As results, they have discovered that the improved tolerance to abiotic stresses may be obtained when expressions of three AtSRP (*Arabidopsis thaliana* stress related protein) genes which encode homologs to the small rubber particle protein (SRPP) in rubber trees (*Hevea brasiliensis*) were increased in plants.

Accordingly, it is an object of this invention to provide a method for improving the tolerance of a plant to an abiotic stress.

It is another object of this invention to provide a method for promoting growth of a plant.

Other objects and advantages of the present invention will become apparent from the following detailed description together with the appended claims and drawings.

BRIEF DESCRIPTION OF THE DRAWINGS

FIG. 1a represents results of analyzing AtSRPs expression by RT-PCR at 7 developmental stages. 18s rRNA was used as a loading control.

WS; whole seedling, RT; root, RL; rosette leaf, ST; stem, F; Flower, SQ; sillique, SD; seed.

Figure 1A:
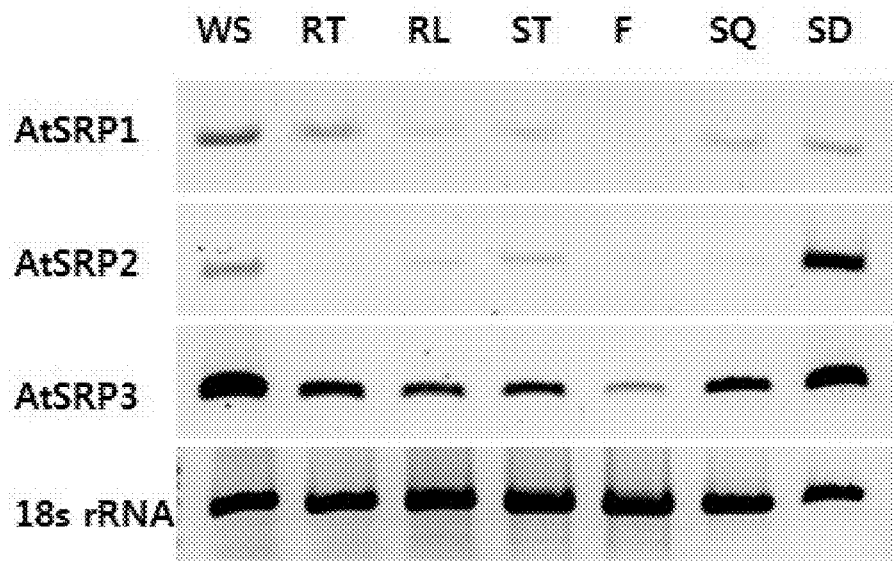
FIGS. 1a and 1b represent that AtSRPs are expressed in various organs of *Arabidopsis*.
Figure 1B:
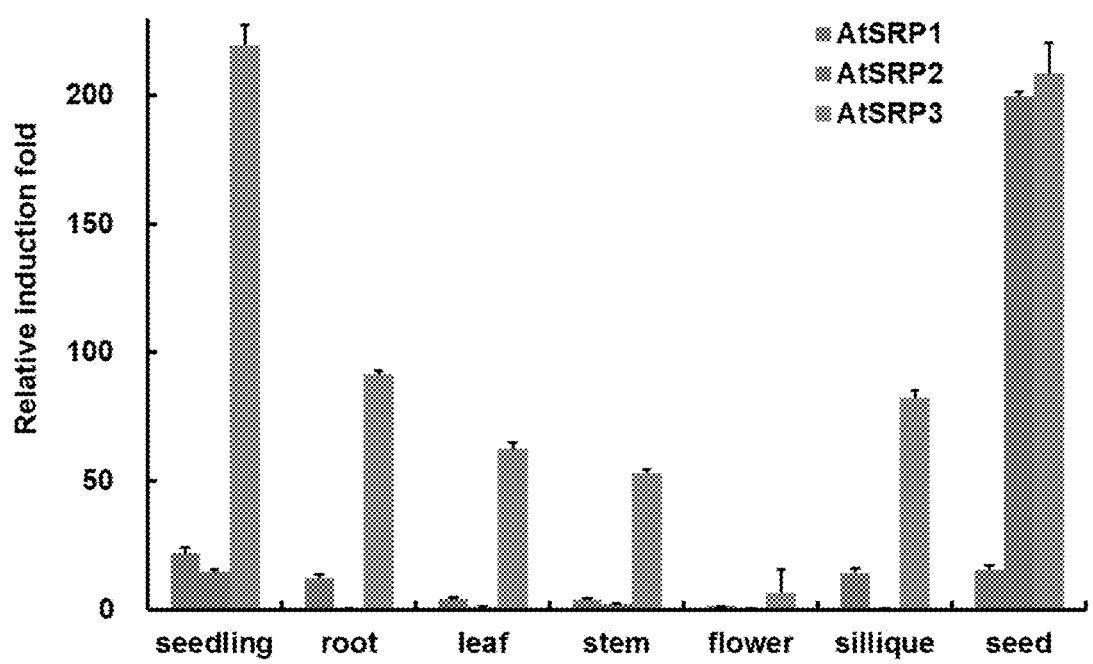

FIG. 1b represents results of analyzing AtSRPs expression by real-time RT-PCR in various organs of *Arabidopsis*. Results are means±S.D. from four repeated experiments.

Figure 2A:
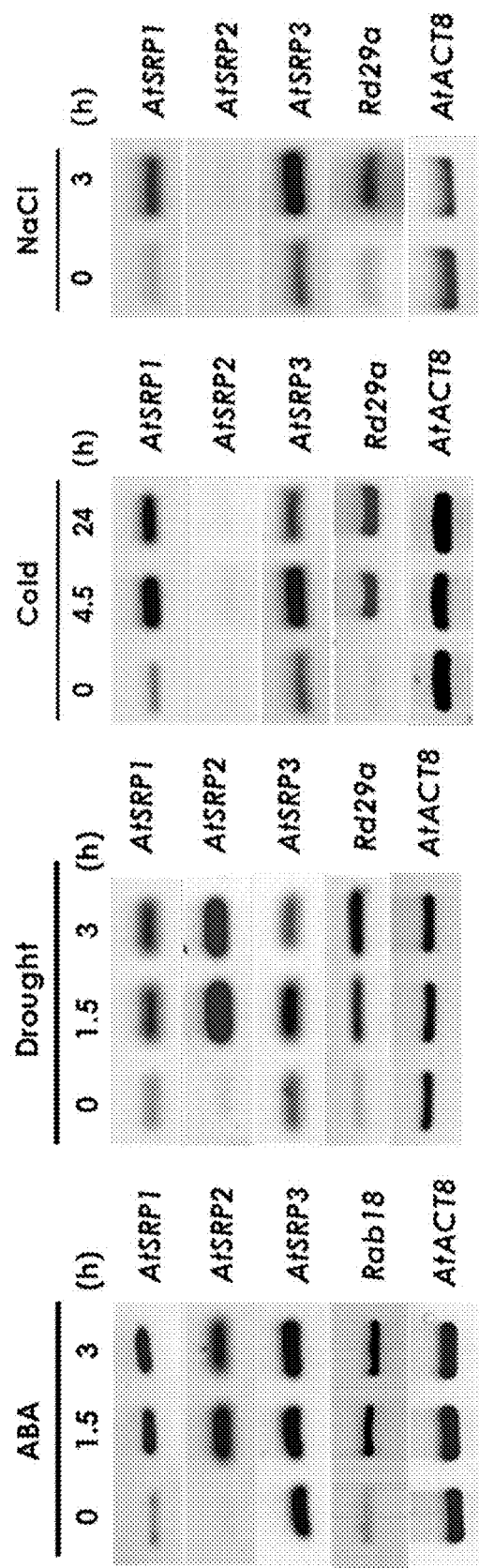
Figure 2B:
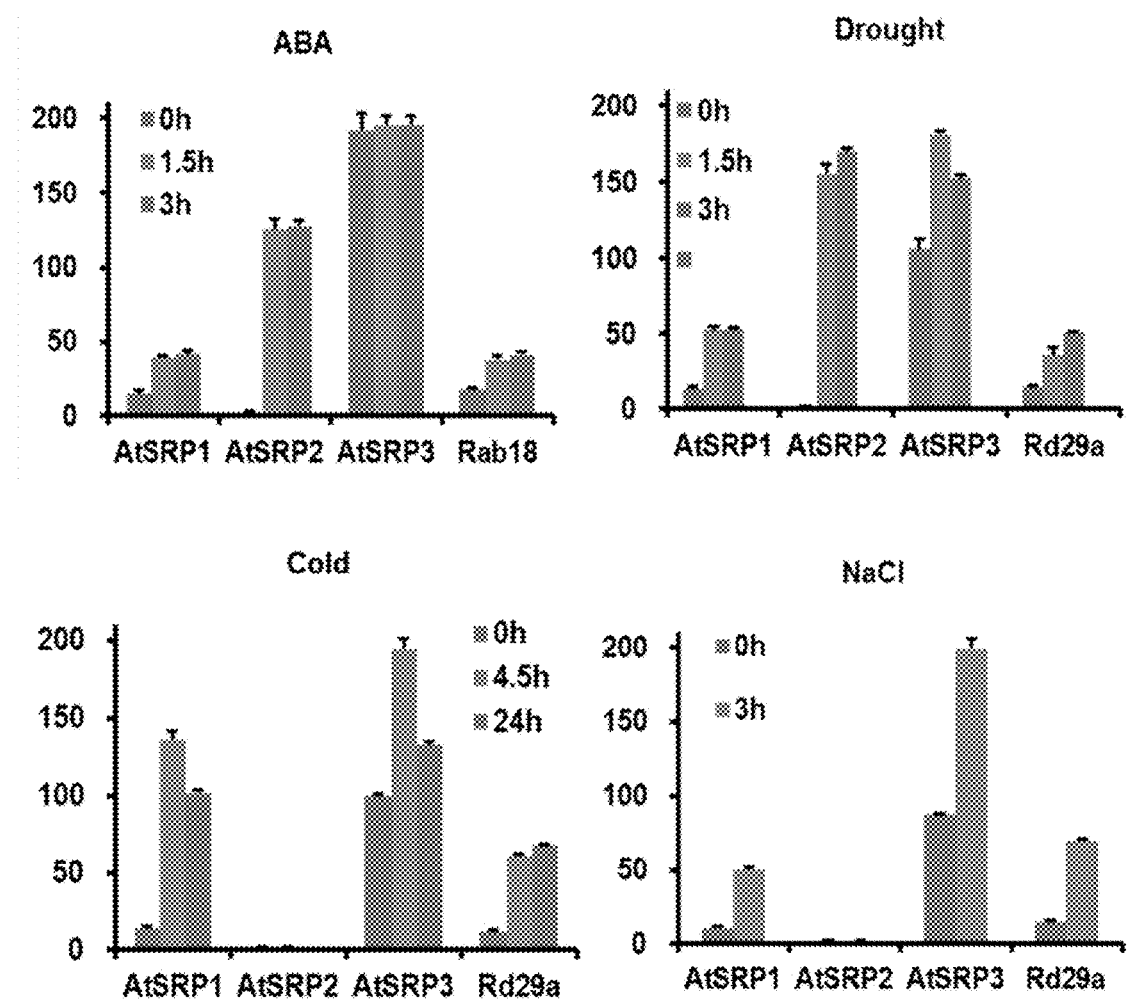

FIGS. 2a and 2b represent that AtSRPs are up-regulated by ABA and abiotic stresses. Total RNA was prepared from light-grown, 7-dold *Arabidopsis* seedlings, which had been treated with 100 mM ABA (1.5-3 hrs), drought (1.5-3 hrs), cold (4° C. for 4.5-24 hrs), or high salinity (300 mM NaCl for 3 hrs). Induction patterns of AtREFPs were investigated by RT-PCR (FIG. 2a) or real-time qRT-PCR (FIG. 2b). The RAB18 and RD29A genes were used as positive controls for ABA and abiotic stress, respectively. AtACT8 transcript levels were used as loading controls. Data represent means±SD from four independent experiments.

Figure 3A:
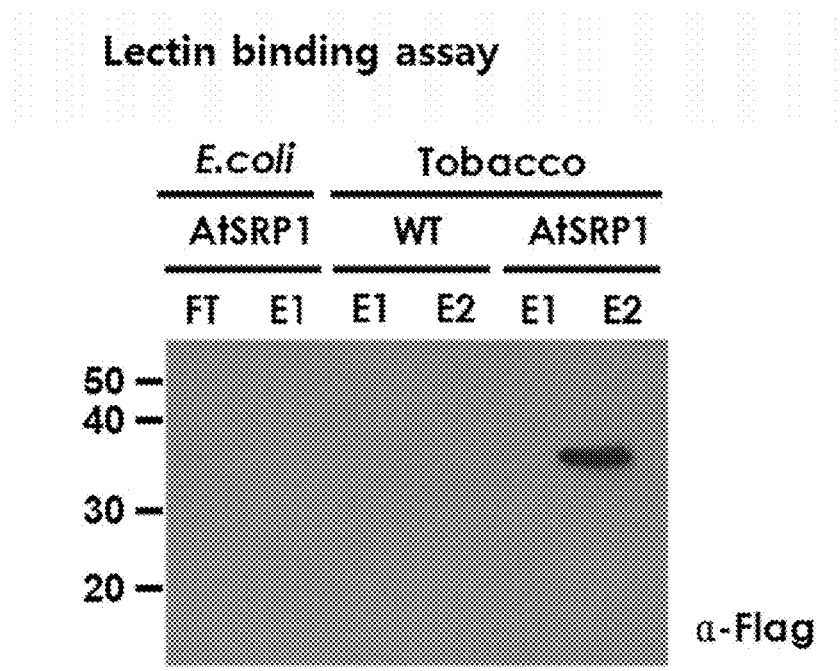
Figure 3B:
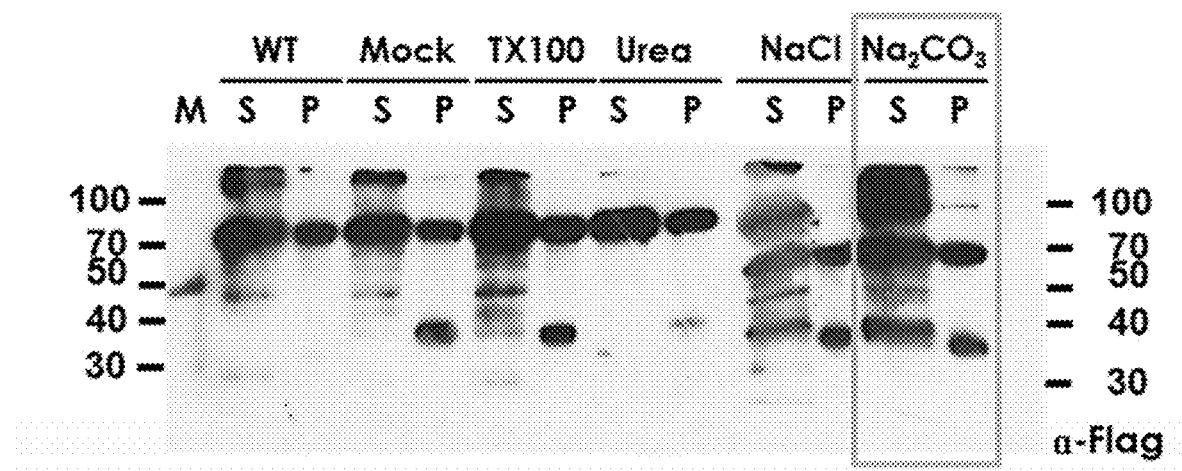

FIGS. 3a and 3b represent that AtSRP1, membrane associated protein, possessed lectin binding property. FIG. 3a represents results of the biochemical analysis using affinity chromatography with concanavalin A. FIG. 3b represents results of the membrane association test. AtSRPs were transiently over-expressed using transient assay. Then, total membrane pellets from *Arabidopsis* seedlings were resuspended in 1% (v/v) Triton X-100, 2 M urea, 1 M NaCl, or 0.1 M $Na_2CO_3$. Suspensions were recentrifuged at 125,000 g to separate solubilized fractions (S) and insoluble fractions (P), which were analyzed by immunoblotting using Flag antibody.

Figure 4A:
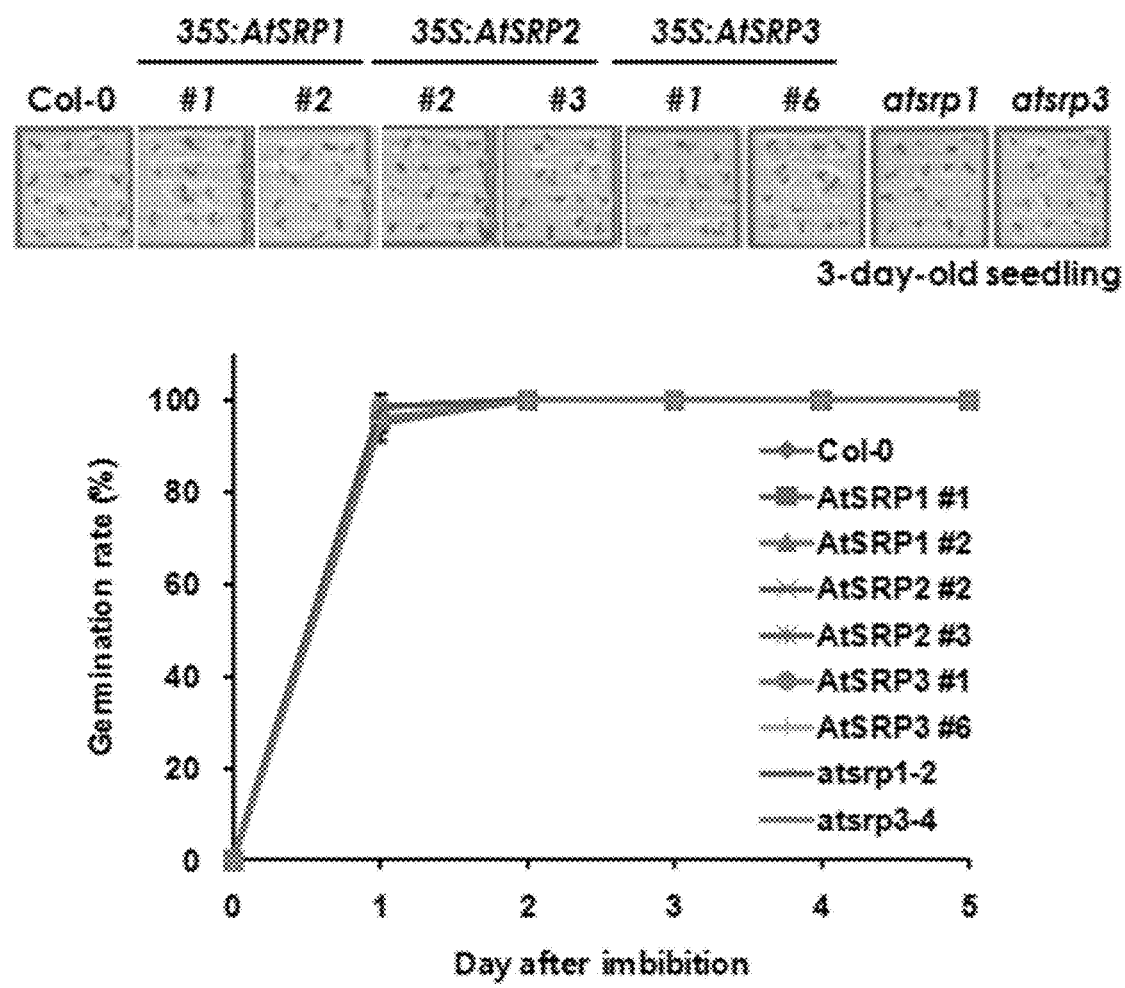
Figure 4B:
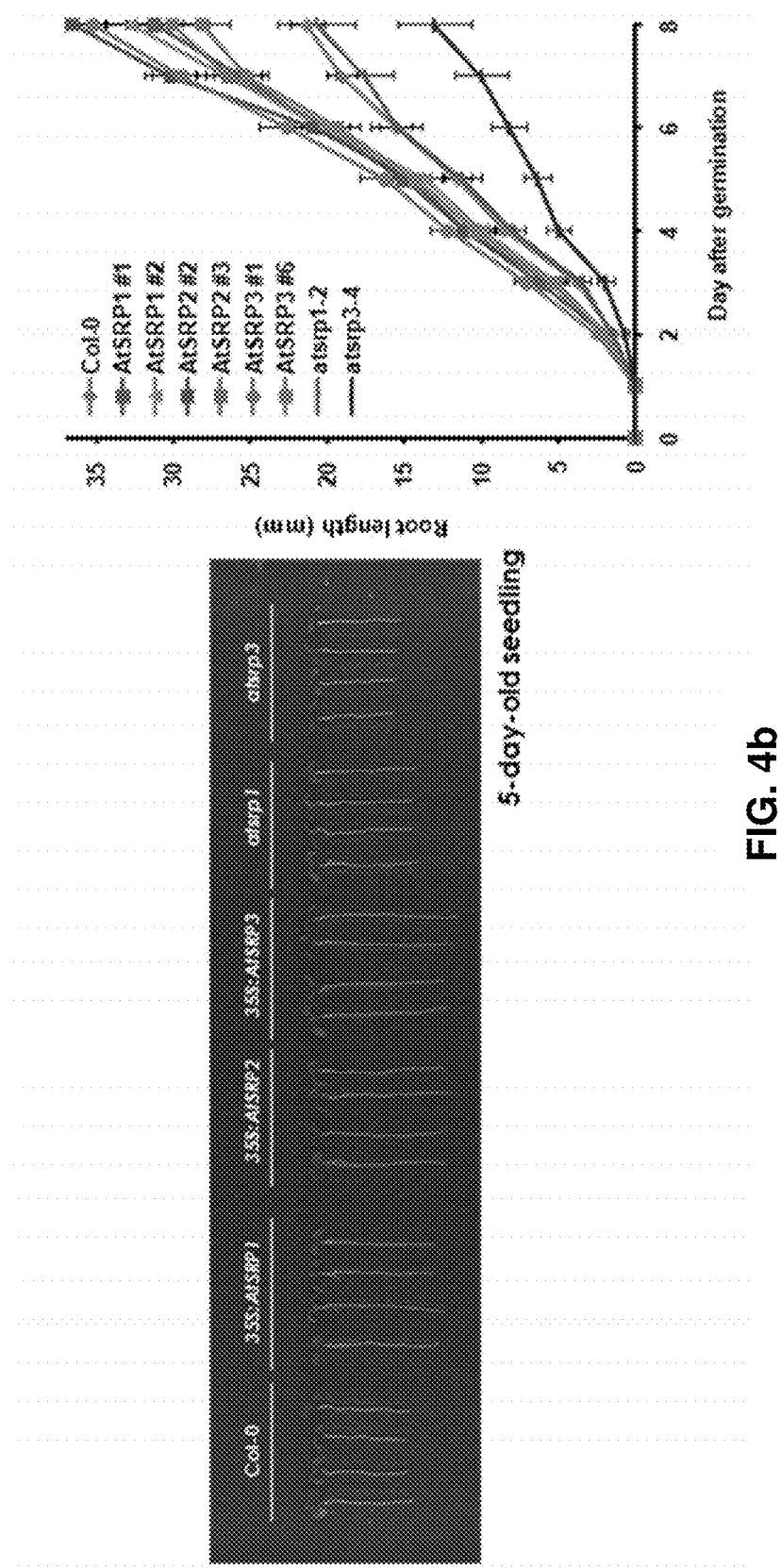
Figure 4C:
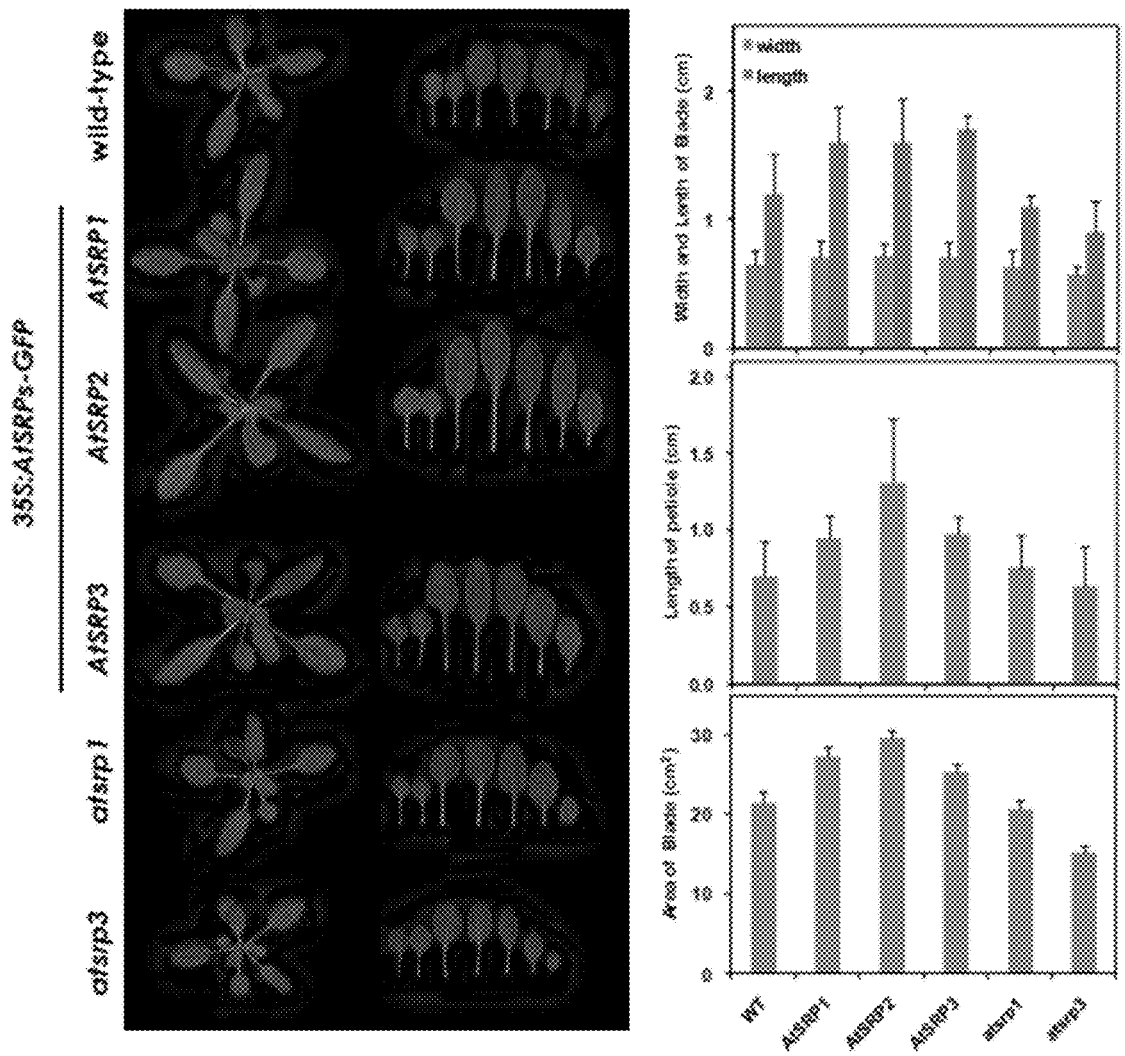
Figure 4D:
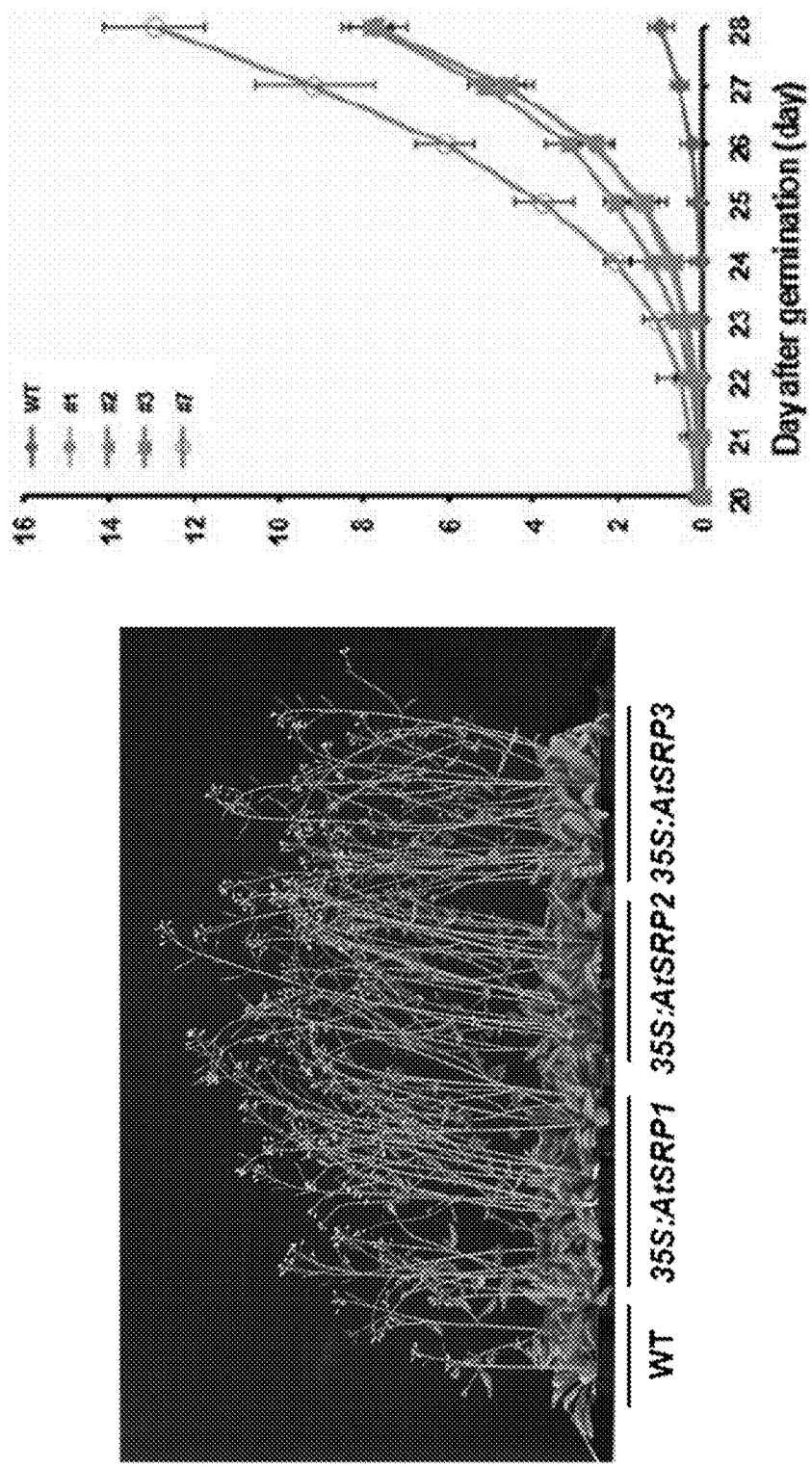

FIG. 4a through 4d represent phenotypic characterizations of T3 35S:AtSRPs transgenic *Arabidopsis* plants and knock-out mutants. AtSRPs-overexpresors grew more rapidly than wild type plants. In contrast, knock-out mutants showed opposite phenotypes. FIG. 4a represents morphological comparisons of light-grown 3-day-old wild type and 35S:AtSRPs transgenic seedlings and knock-out mutants. FIG. 4b represents differences in growth patterns of early roots in wild type, AtSRPPs-overexpressing, and knock-out seedlings. Error bars indicate mean±SD (n=70). FIG. 4c represents determination of the dimensional parameters of second leaves 2 weeks after germination. The second leaves were detached from wild type, transgenic, and knock-out mutant lines, scanned for image analysis using SCIONIMAGE program, and their blade widths and lengths, petiole lengths, and blade areas were calculated. Error bars indicate mean±SD (n=35). FIG. 4d represents growth morphology of wild type, 35S:AtSRPs transgenic *Arabidopsis*, and knock-out mutant plants grown under normal growth conditions 28 days after germination (left panel). Right panel represents differences in growth patterns of inflorescence stems of wild type and transgenic *Arabidopsis* plants 20 to 28 days after germination. Error bars indicate mean±SD (n=80).

Figure 5A:
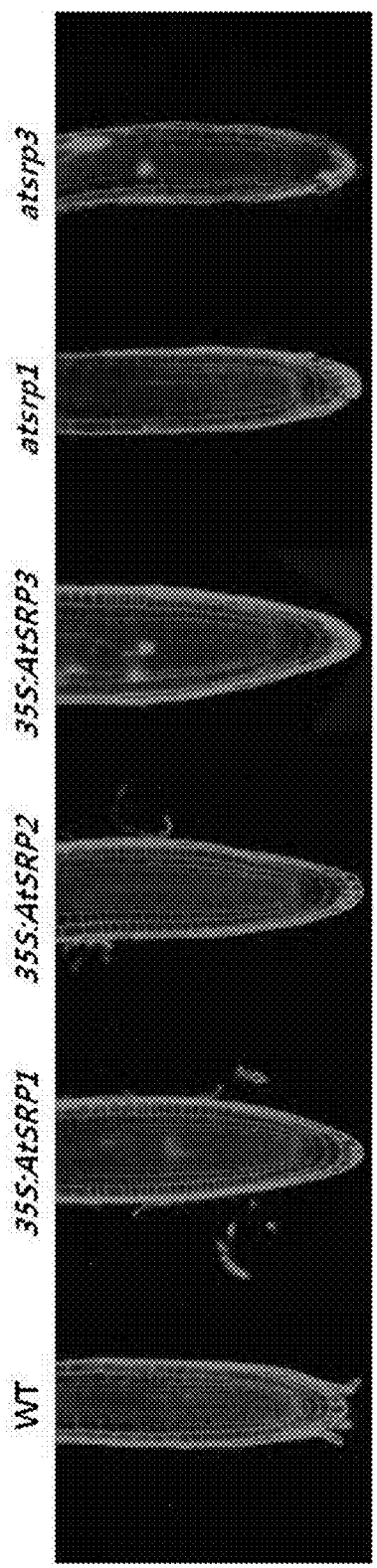
Figure 5B:
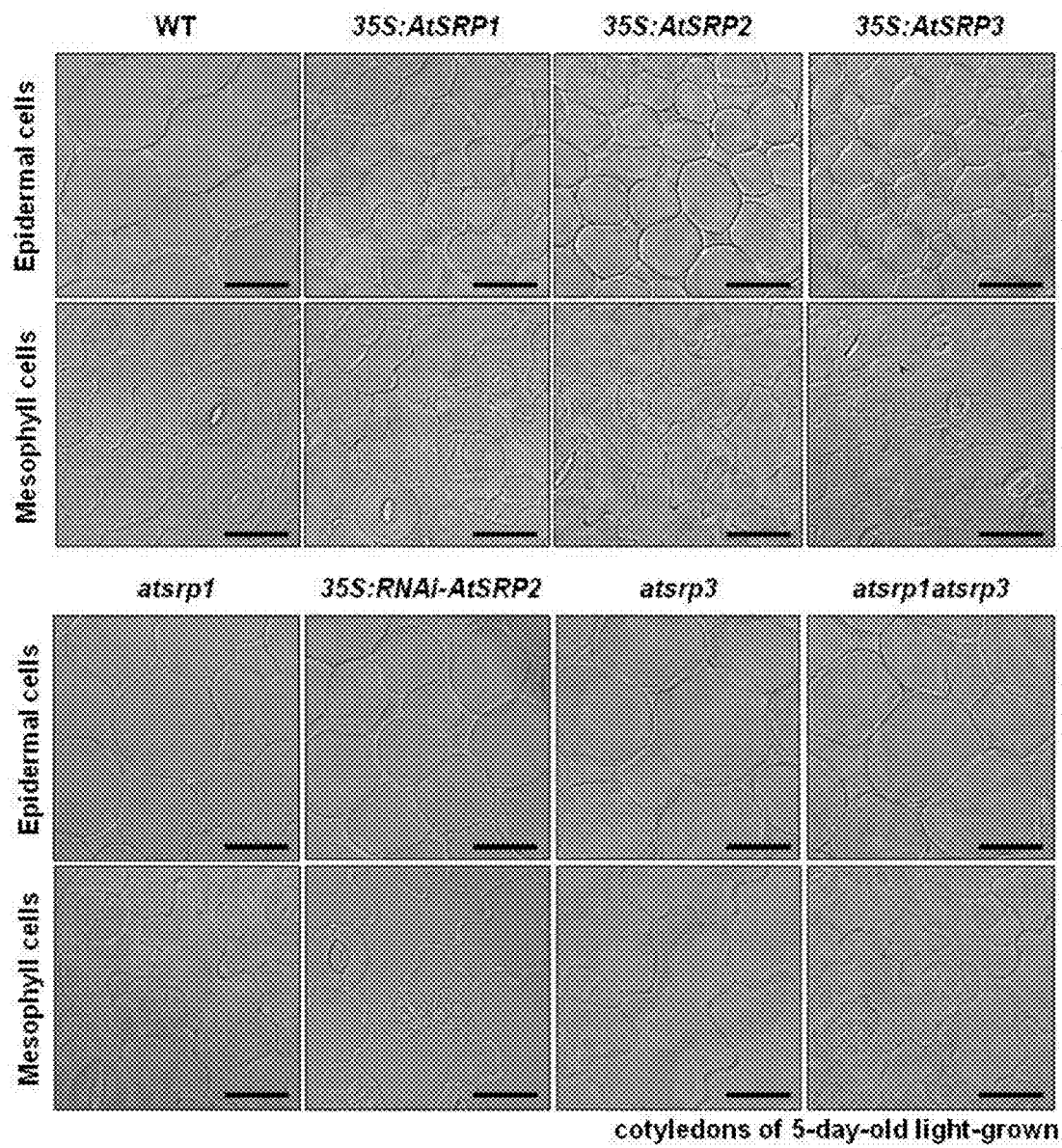

FIGS. 5a and 5b represent faster-growing phenotypes of 35S:AtSRPs transgenic plants correlated with enhanced cell cycle progression. FIG. 5a represents longitudinal views of root tips from 3-day-old wild type and AtSRPs-overexpressing transgenic and knock-out mutant seedlings. Root sections were stained with propidium iodide and analyzed by confocal microscopy. FIG. 5b represents results of confocal microscope demonstrating the epidermal and palisade mesophyll cells from the second leaves of wild type, AtSRPs-overexpressors, and knock-out mutants. Scale bars=20 μm.

Figure 6:
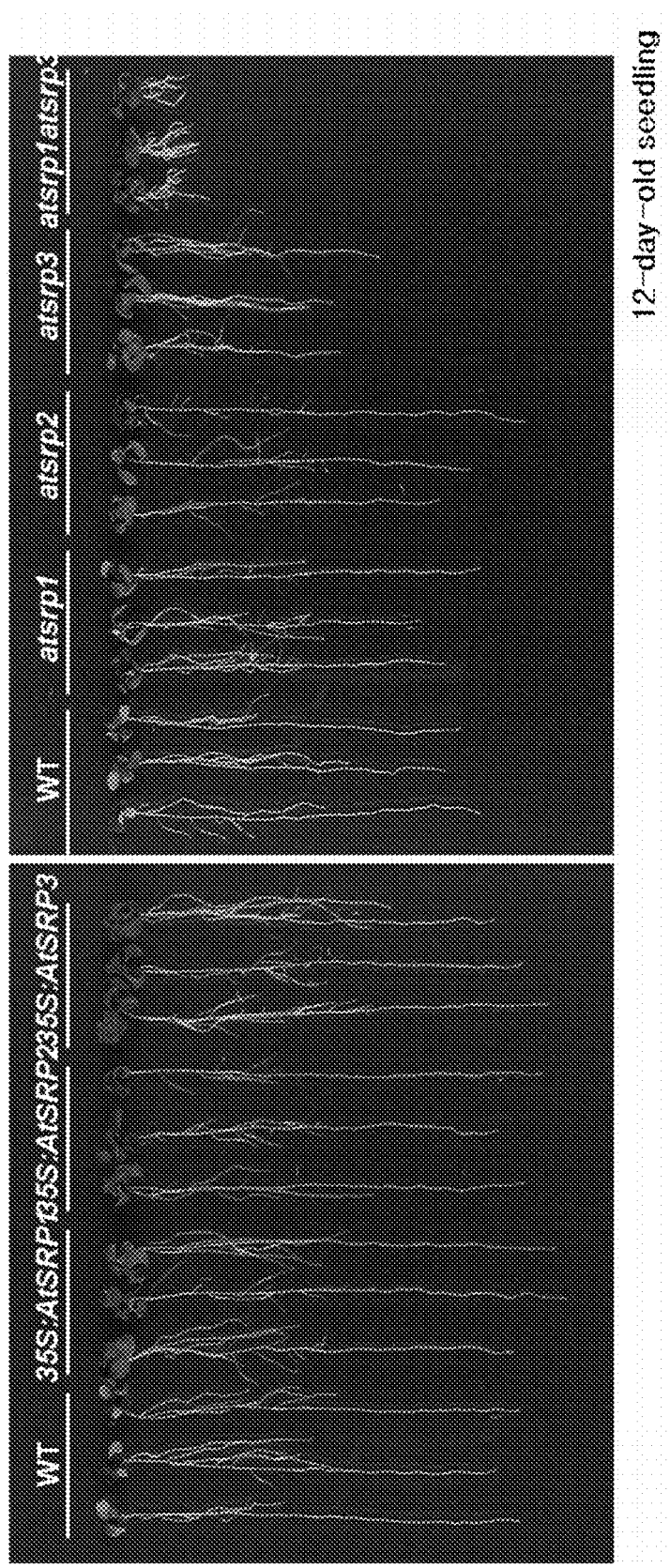

FIG. 6 represents that loss of function of AtSRPs showed susceptible phenotype against salt stress. It shows morphologies of 12-day-old wild-type, AtSRPs-overexpressing transgenic, and knock-out mutant seedlings in 100 mM NaCl media.

Figure 7A:
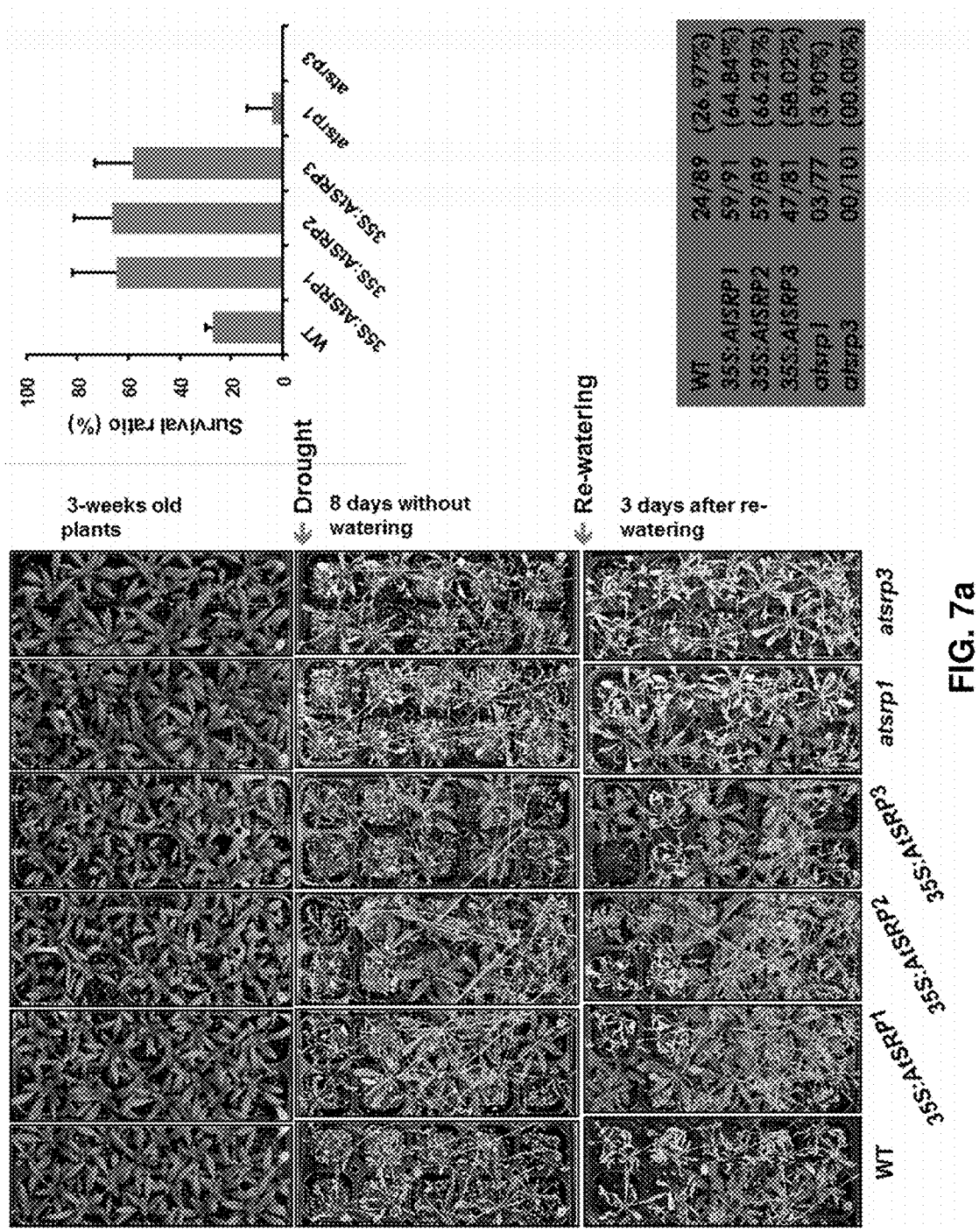
Figure 7B:
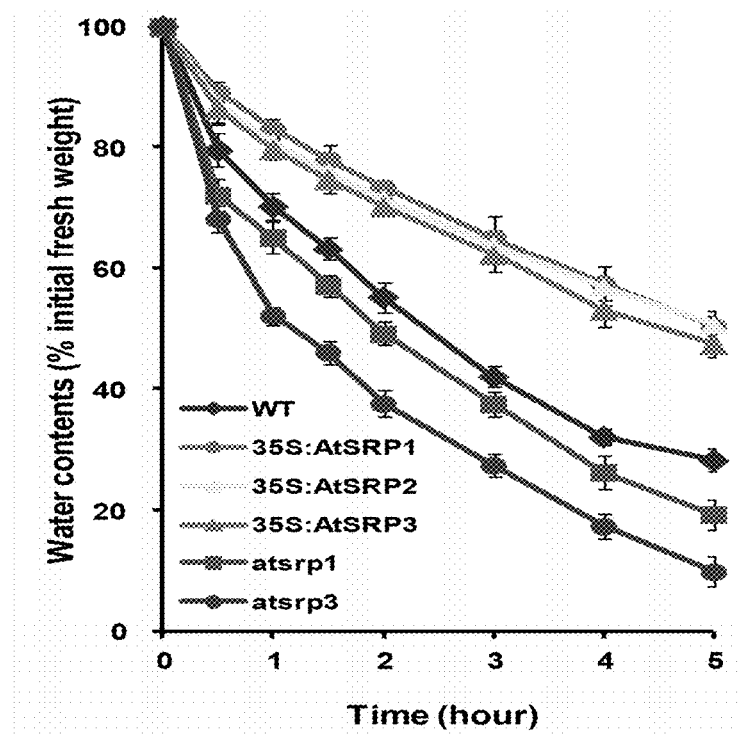
Figure 7C:
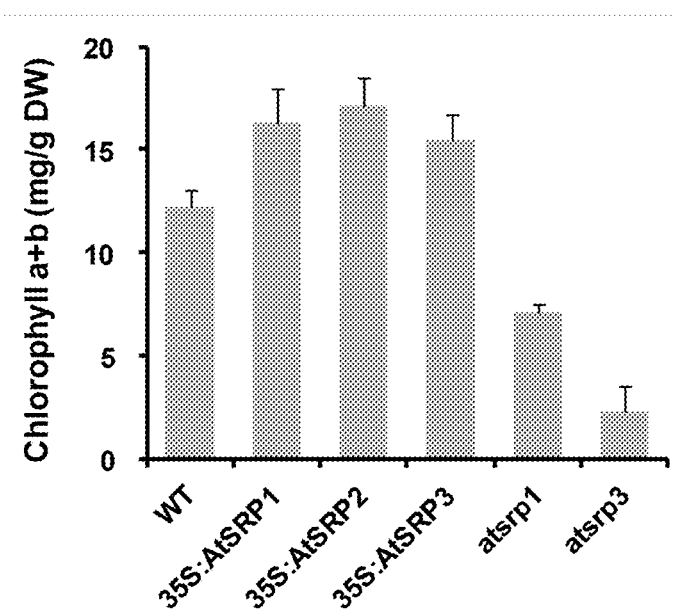

FIG. 7a through 7c represent that AtSRPs play a role as a positive factor for drought defensive responses. FIG. 7a represents survival rates of wild type and 35S:AtSRPs transgenic plants after drought stress. Light-grown 25-day-old wild type, 3-week-old transgenic plants, and 26-day-old knock-out mutants were further grown for 8 days without watering. Plants were then re-watered and their survival rates were determined after 3 days. The survival rate was considered as the ability of plants to continue to grow after returned to normal water conditions following eight-day drought stress. The survival rates are following: wild type, 26.97% (24 out of 89 plants); 35S:AtSRP1 transgenic line, 64.84% (59 out of 91 plants); 35S:AtSRP2 transgenic line, 66.29% (59 out of 89 plants); 35S:AtSRP3 transgenic line, 58.02% (47 out of 81 plants); atsrp1 mutant line, 3.90% (3 out of 77 plants) and atsrp3 mutant line, 0.00% (0 out of 101 plants). FIG. 7b represents results of measurement of cut rosette water loss (CRWL) rates. The rosette leaves were detached from light-grown 3-week-old wild type, 35S:AtSRPs transgenic plants, and knock-out mutants, placed on open-lid Petri dishes, and incubated for 0-5 hrs at room temperature. Decreases in fresh weights were determined. Water loss is expressed as the percentage of initial fresh weight of the detached leaves. Error bars indicate mean±SD (n=20). FIG. 7c represents amount (mg/g DW) of chlorophyll a+chlorophyll b in leaves of wild, 35S:AtSRPs-over-expressing plants, and knock-out mutants. Error bars indicate mean±SD (n=3).

Figure 8:
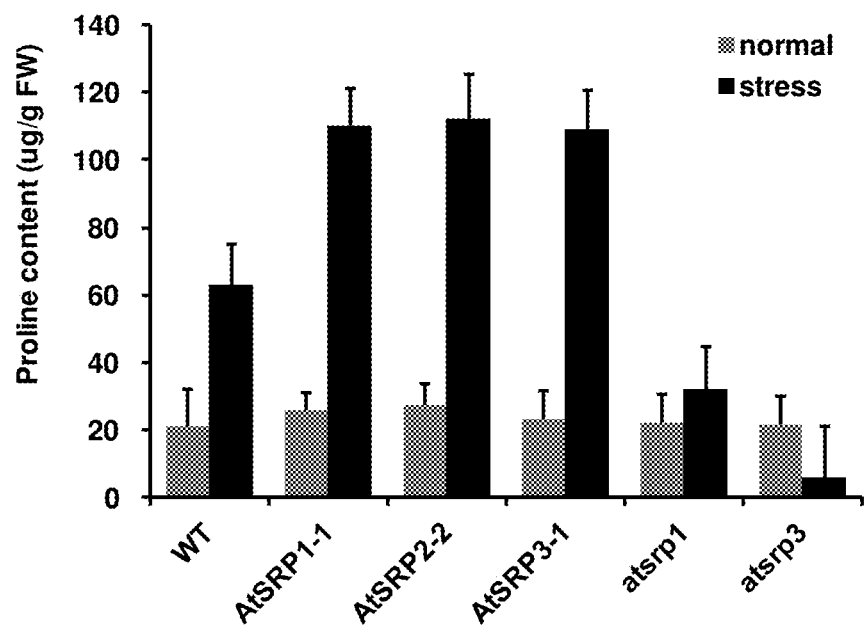

FIG. 8 represents analysis results of proline content of leaf discs before and after drought treatments. Data were obtained from three independent experiments. Bars represent means±SD (n=3). 35S:AtSRPs transgenic leaves retained their leaf water more effectively than did wild-type leaves under drought conditions. In contrast, knockout mutants showed opposite phenotypes.

Figure 9:
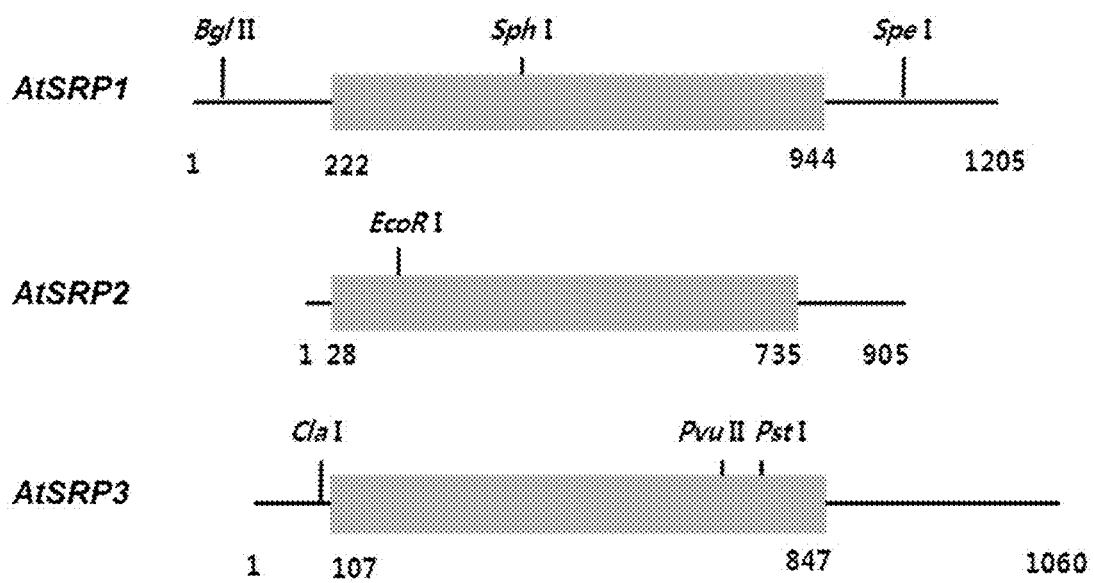

FIG. 9 schematically represents AtSRP1, AtSRP2 and AtSRP3 cDNA clones.

DETAILED DESCRIPTION OF THE INVENTION

In one aspect of this invention, there is provided a method for improving the tolerance of a plant to an abiotic stress, comprising:

(a) introducing a nucleotide sequence encoding the amino acid sequence selected from the group consisting of SEQ ID NOs:4 to 6 to a cell of the plant; and (b) obtaining a transgenic plant exhibiting improved tolerance to an abiotic stress from the cell of the plant.

The present inventors have made intensive studies to increase the productivity of crop plants by developing genes for improving a tolerance to abiotic stresses including drought, high salt and cold of the plants. As results, they have discovered that the improved tolerance to abiotic stresses may be obtained when expressions of three AtSRP (*Arabidopsis thaliana* stress related protein) genes which encode homologs to the small rubber particle protein (SRPP) in rubber trees (*Hevea brasiliensis*) were increased in plants.

According to a preferred embodiment, the present nucleotide sequence encoding the amino acid sequence of SEQ ID NOs:4, 5 and 6 comprises the nucleotide sequence as set forth in SEQ ID NO:1, 2 and 3, respectively.

According to a preferred embodiment, the amino acid sequence of SEQ ID NOs:4, 5 and 6 is the sequence of SRPP-like proteins present in *Arabidopsis*. These proteins are named as AtSRP (*Arabidopsis thaliana* stress related protein) 1, AtSRP 2 and AtSRP 3, respectively. As shown in Examples, the present inventors have found that expressions of these proteins or their coding genes were increased by various abiotic stresses, and the improved tolerance to abiotic stresses may be obtained when these genes were over-expressed in plants.

It would be obvious to the skilled artisan that the nucleotide sequences used in this invention are not limited to those listed in the appended Sequence Listings. The nucleotide sequences described herein are illustrative and their biological equivalents may be also used in this invention for enhancement of tolerance to a drought stress and promotion of flowering or growing in plants. In this regard, the sequence variations should be construed to be covered by the present invention.

For nucleotides, the variations may be purely genetic, i.e., ones that do not result in changes in the protein product. This includes nucleic acids that contain functionally equivalent codons, or codons that encode the same amino acid, such as six codons for arginine or serine, or codons that encode biologically equivalent amino acids.

Considering biologically equivalent variations described hereinabove, the nucleic acid molecule of this invention may encompass sequences having substantial identity to them. Sequences having the substantial identity show at least 80%, more preferably at least 90%, most preferably at least 95% similarity to the nucleic acid molecule of this invention, as measured using one of the sequence comparison algorithms. Methods of alignment of sequences for comparison are well-known in the art. Various programs and alignment algorithms are described in: Smith and Waterman, *Adv. Appl. Math.* 2:482 (1981); Needleman and Wunsch, *J. Mol. Bio.* 48:443 (1970); Pearson and Lipman, *Methods in Mol. Biol.* 24: 307-31 (1988); Higgins and Sharp, *Gene* 73:237-44 (1988); Higgins and Sharp, *CABIOS* 5:151-3 (1989) Corpet et al., *Nuc. Acids Res.* 16:10881-90 (1988) Huang et al., *Comp. Appl. BioSci.* 8:155-65 (1992) and Pearson et al., *Meth. Mol. Biol.* 24:307-31 (1994). The NCBI Basic Local Alignment Search Tool (BLAST) [Altschul et al., *J. Mol. Biol.* 215:403-10 (1990)] is available from several sources, including the National Center for Biological Information (NBCI, Bethesda, Md.) and on the Internet, for use in connection with the sequence analysis programs blastp, blasm, blastx, tblastn and tblastx. It can be accessed at www.ncbi.nlm.nih.gov/BLAST/. A description of how to determine sequence identity using this program is available at www.ncbi.nlm.nih.gov/BLAST/blast_help.html.

According to a preferred embodiment, the abiotic stress is selected from the group consisting of a drought stress, a low-temperature stress and a salt stress.

To introduce a foreign nucleotide sequence into plant cells or plants may be performed by the methods (*Methods of Enzymology*, Vol. 153, 1987) known to those skilled in the art. The plant may be transformed using the foreign nucleotide inserted into a carrier (e.g., vectors such as plasmid or virus) or *Agrobacterium tumefaciens* as a mediator (Chilton et al., *Cell*, 11: 263-271 (1977)) and by directly inserting the foreign nucleotide into plant cells (Lorz et al., *Mol. Genet.*, 199: 178-182 (1985); the disclosure is herein incorporated by reference). For example, electroporation, microparticle bombardment, polyethylene glycol-mediated uptake may be used in the vector containing no T-DNA region.

Generally, *Agrobacterium*-mediated transformation is the most preferable (U.S. Pat. Nos. 5,004,863, 5,349,124 and 5,416,011), and the skilled artisan can incubate or culture the transformed cells or seeds to mature plants in appropriate conditions.

The term "plant(s)" as used herein, is understood by a meaning including a plant cell, a plant tissue and a plant seed as well as a mature plant.

The plants applicable of the present invention include, but not limited to, food crops such as rice plant, wheat, barley, corn, bean, potato, Indian bean, oat and Indian millet; vegetable crops such as *Arabidopsis* sp., Chinese cabbage, radish, red pepper, strawberry, tomato, watermelon, cucumber, cabbage, melon, pumpkin, welsh onion, onion and carrot; crops for special use such as ginseng, tobacco plant, cotton plant, sesame, sugar cane, sugar beet, *Perilla* sp., peanut and rape; fruit trees such as apple tree, pear tree, jujube tree, peach tree, kiwi fruit tree, grape tree, citrus fruit tree, persimmon tree, plum tree, apricot tree and banana tree; flowering crops such as rose, gladiolus, gerbera, carnation, chrysanthemum, lily and tulip; and fodder crops such as ryegrass, red clover, orchardgrass, alfalfa, tallfescue and perennial ryograss.

According to a preferred embodiment, the nucleotide sequence is contained a recombinant plant expression vector; and the recombinant plant expression vector comprises (i) the nucleotide sequence; (ii) a promoter which is operatively linked to the nucleotide sequence of (i) and generates RNA molecules in plant cells; and (iii) a poly A signal sequence inducing polyadenylation at the 3'-end of the RNA molecules.

The term "operatively linked" as used herein refers to functional linkage between a nucleic acid expression control sequence (such as a promoter, signal sequence, or array of transcription factor binding sites) and a second nucleotide sequence, wherein the expression control sequence affects transcription and/or translation of the nucleic acid corresponding to the second sequence.

The vector system of this invention may be constructed in accordance with conventional techniques described in Sambrook et al., *Molecular Cloning, A Laboratory Manual*, Cold Spring Harbor Laboratory Press (2001), teachings of which are incorporated herein by reference.

The suitable promoter in the present invention includes any one commonly used in the art, for example SP6 promoter, T7 promoter, T3 promoter, PM promoter, maize-ubiquitin promoter, Cauliflower mosaic virus (CaMV)-35S promoter, Nopalin synthase (nos) promoter, Figwort mosaic virus 35S promoter, Sugarcane bacilliform virus promoter, commelina yellow mottle virus promoter, photo-inducible promoter of small subunit of Ribulose-1,5-bis-phosphate carboxylase (ssRUBISCO), cytosolic triosphosphate isomerase (TPI) promoter in rice, adenine phosphoribosyl-transferase (APRT) or octopine synthase promoter in *Arabidopsis*. Preferably, the promoter used in this invention is CaMV 35S.

According to a preferred embodiment, the 3'-non-translated region causing polyadenylation includes that from the nopaline synthase gene of *Agrobacterium tumefaciens* (NOS 3' end) (Bevan et al., *Nucleic Acids Research*, 11(2):369-385 (1983)), that from the octopine synthase gene of *Agrobacterium tumefaciens*, the 3'-end of the protease inhibitor I or II genes from potato or tomato, the CaMV 35S terminator, and OCS (octopine synthase) terminator. Most preferably, the 3'-non-translated region causing polyadenylation in this invention is NOS.

Optionally, the present vector for plants may further carry a reporter molecule (e.g., genes for luciferase and β-glucuronidase). In addition, the vector may contain antibiotic resistant genes as selective markers (e.g., neomycin phosphotransferase gene (nptII) and hygromycin phosphotransferase gene (hpt)).

According to a preferred embodiment, the plant expression vector of this invention is *Agrobacterium* binary vectors.

The term "binary vector" as used herein, refers to a cloning vector containing two separate vector systems harboring one plasmid responsible for migration consisting of left border (LB) and right border (RB), and another plasmid for target gene-transferring. Any *Agrobacterium* suitable for expressing the nucleotide of this invention may be used, and most preferably, the transformation is carried out using *Agrobacterium tumefaciens* GV3101.

Introduction of the recombinant vector of this invention into *Agrobacterium* can be carried out by a large number of methods known to one skilled in the art. For example, particle bombardment, electroporation, transfection, lithium acetate method and heat shock method may be used. Preferably, the electroporation is used.

According to the present invention, the present AtSRPs-overexpressing transgenic plants grew more rapidly with longer roots, larger leaves, and bolted earlier with prolonged inflorescences. The growth rates of the transgenic plants are enhanced using properties of the AtSRPs genes, whereby they may effectively applied for cultivating the plants with novel function of rapid growing, and biomass.

In another aspect of this invention, there is provided a method for promoting the growth of a plant, comprising:

(a) introducing a nucleotide sequence encoding the amino acid sequence selected from the group consisting of SEQ ID NOs:4 to 6 to a cell of the plant; and (b) obtaining a transgenic plant exhibiting improved tolerance to an abiotic stress from the cell of the plant.

As the present amino acid sequence, the present nucleotide sequence and the plant expression vector comprising thereof are mentioned above, they are omitted herein to avoid excessive overlaps.

The features and advantages of the present invention will be summarized as follows:

(a) The present invention provides a method for improving the tolerance of a plant to an abiotic stress and a method for promoting growing of a plant.

(b) The present nucleotide sequence is involved in abiotic stress tolerance such as drought, low-temperature and salt stresses of plants. Therefore, the overexpressing transgenic plants have excellent tolerances to these abiotic stresses, whereby they may be useful as novel functional crops which are affected by climates and environments of the cultivated areas.

(c) In addition, where the plants are transformed with the present nucleotide sequence, the growth abilities of the transgenic plants are remarkably enhanced, whereby they may effectively used for cultivating the plants with novel function of rapid growing, and biomass.

The present invention will now be described in further detail by examples. It would be obvious to those skilled in the art that these examples are intended to be more concretely illustrative and the scope of the present invention as set forth in the appended claims is not limited to or by the examples.

Examples

Cloning and Analysis of AtSRPs Gene

Total mRNA was extracted from 5-day-old *Arabidopsis thaliana* seedlings to perform RT-PCT (Seo et al., 2008). cDNA was synthesized by reverse transcription. To amplify specifically AtSRP1, AtSRP2 and AtSRP3 genes, primer pairs used in PCR were prepared by searching cDNA sequence to each of AtSRP1, AtSRP2 and AtSRP3 genes from a database of the *Arabidopsis* Information Resource (TAIR, www.arabidopsis.org), and subsequently, tagging BamHI at CDS 5' and SacI at CDS 3'. Each of the amplified cDNA of AtSRP1, AtSRP2 and AtSRP3 gene was ligated to pGEM-T Easy vector (Promega, www.promega.com) to cloning, and the sequence was analyzed by sequencing reaction (Table 1). The analyzed sequence was exactly corresponded with that of TAIR (www.arabidopsis.org). In addition, it was found that At1g67360 (AtSRP1) included CDS consisting of 723 bp, At2g47780 (AtSRP2) included CDS consisting of 708 bp, and At3g05500 (AtSRP3) included CDS consisting of 741 bp.

Expression Analysis of AtSRPs Genes

To analyze the AtSRPs expression in transcription level in various tissues, RT-PCR and real-time RT-PCR were performed (Seo et al., 2008). Primers used in the analysis are shown in Table 1.

TABLE 1

Primers for cloning, preparations of transgenic plants, and protein expressions

| Gene | Forward primer | Reverse primer |
|---|---|---|
| Cloning of AtSRPs ORF, RT-PCR and preparation of transgenic plant | | |
| AtSRP1 | 5'-gcggatccatggagacagagaagaaaaatag-3' (SEQ ID NO: 7) | 5'-gcgagctcctactccgaatcagacgatg-3' (SEQ ID NO: 8) |
| AtSRP2 | 5'-gcggatccatggctgaagatgaaatagtagtc-3' (SEQ ID NO: 9) | 5'-gcgagctctcaatcagctcgacactgatc-3' (SEQ ID NO: 10) |
| AtSRP3 | 5'-gcggatccatggctactcaaacggatctc-3' (SEQ ID NO: 11) | 5'-gcgagctctcaatcaagtggatggaactc-3' (SEQ ID NO: 12) |
| 18s rRNA | 5'-gcatttgccaaggatgtttt-3' (SEQ ID NO: 13) | 5'-gtacaaagggcagggacgta-3' (SEQ ID NO: 14) |
| AtACT8 | 5'-tactgattacctcatgaagatccttac-3' (SEQ ID NO: 15) | 5'-aaacgatgtctctttagtttagaagc-3' (SEQ ID NO: 16) |
| Quantitative real time RT-PCR primer | | |
| AtSRP1 | 5'-tgattctctcctggtctttc-3' (SEQ ID NO: 17) | 5'-ttctctgtcgccttgtagat-3' (SEQ ID NO: 18) |
| AtSRP2 | 5'-ttttcgtcgatcgtaagg-3' (SEQ ID NO: 19) | 5'-aatgctcttggtagtgtcca-3' (SEQ ID NO: 20) |
| AtSRP3 | 5'-ccctgttgaggtccttaaat-3' (SEQ ID NO: 21) | 5'-gccacaatgggtgctat-3' (SEQ ID NO: 22) |

Expression and Purification of AtSRPs Proteins

AtSRPs were fused with 2×Flag epitope, expressed to BL21-CodonPlus (DE3) RIL (Stratagene), and purified. The proteins were quantified using BSA as a standard protein (Bradford, 1976).

Measurement for Lectin Binding Properties of AtSRPs

To investigate binding properties to lectin of AtSRPs, two proteins were used as follows: 2×Flag-AtSRPs were expressed in *E. coli*, and purified to obtain protein; and 35S:2×Flag-AtSRPs were transiently over-expressed in tobacco to obtain protein.

The two proteins were subject to concanavalin A binding assay according to the manufacturer's method (Con A Sepharose 4B-GE-71707700AG; GEHealthcare Life Sciences). The resultants were subject to immunoblotting using Flag antibodies. As a result, the only band was elucidated in the lane of 35S:2×Flag-AtSRPs using tobacco system, indicating that the only AtSRP1 glycosylated in plant system binds to lectin. Accordingly, it would be understood that the AtSRP1 is a glycoprotein (FIG. 3a).

Measurement for Membrane Association Properties of AtSRPs

To investigate association properties to membrane of AtSRPs, 35S:2×Flag-AtSRPs were transiently over-expressed in tobacco to obtain protein. The protein was extracted to use. Then, the protein was subject to membrane association test according to Kim and Bassham (Kim and Bassham, 2011). The resultants were subject to immunoblotting using Flag antibodies. As a result, the band of the supernatant in the 0.1 M $Na_2CO_3$-treated membrane pellet was darker than that of the precipitate (FIG. 3b), addressing that the AtSRP1 protein binding to membrane was eluted into the supernatant by $Na_2CO_3$ that weakens binding of the AtSRP1 protein to membrane. Accordingly, it would be understood that AtSRPs proteins are membrane associated proteins.

Preparation of AtSRPs-Overexpressing Transgenic Plants and Identification of Knock-Out Mutants The AtSRPs cDNA were introduced into the corresponding sites of the binary vector pBI121 to overexpress. The used primers are shown in Table 1. The resulting fusion gene was transferred to *Agrobacterium tumefaciens*. *Agrobacterium* cells were transformed into *Arabidopsis* plants by means of the floral-dip method (Joo et al., 2004). Seeds were germinated on 0.5× Murashige and Skoog (MS) medium with 30 µg/ml kanamycin to select independent transgenic plants. atsrp1 and atsrp3 used T-DNA insertion lines (atsrp1: GABI_3095G05, atsrp3: WiscDSLOXHS192) which were purchased from ABRC (www.arabidopsis.org). atsrp2 used knock-down line, which is prepared by RNAi method, to select plants in which expression in transcription level is lower (Lee and Kim, 2010).

Phenotypic Analyses of AtSRPs-Overexpressing Transgenic Plants

Medium was prepared to contain 0.5×MS (including vitamin B5), 1% sucrose and 0.8% agar (select agar; Life Technology, Rockville, Md., USA) (pH 5.7). Surfaces of seeds of wild type plants and AtSRPs-overexpressing transgenic plants were sterilized, planted and grown under light condition at 22° C. After inhibition of radicle germination, they were daily observed for 5 days. In order to observe the root growth, seeds were observed until 5th day after germination. During the root growth, the root shoot-tip was marked in outside of culture plates, and the root length was measured using ScionImage software (Scion Corp., Frederic, Md., USA). In order to observe the leaf size, the seeds were planted in sterile soil. After 12 days, sizes of the leaves from a seed leaf to a third leaf in wild type plants and AtSRPs-overexpressing transgenic plants were compared. In addition, the second leaf was measured in leaf length, leaf width and petiole length using ScionImage software (Scion Corp., Frederic, Md., USA).

In order to observe the flower stalk rising time, seeds of wild type plants and overexpressing transgenic plants were planted in sterile soil, and grown under light condition at 22° C. At 19 days after germination, the flower stalk length was measured. As a result, when wild type plants and AtSRPs-overexpressing transgenic plants were compared each other, there was no difference in germination ability. However, AtSRPs-overexpressing transgenic plants grew more rapidly with longer roots, larger leaves, and longer height. Therefore, it could be demonstrated that AtSRPs act as a positive regulator in plant growth (FIGS. 4a-d).

Phenotypic Analyses Using Microscope

Leaves of 5-day-old wild-type and transgenic *Arabidopsis thaliana* were washed in a solution of chloral hydrate with the reported method (Kwon et al. 2009). Cell layer was observed by bright-field microscope (BX51 fluorescence microscope, Olympus, Japan). For longitudinal views of root tips, roots of 5-day-old wild-type and transgenic *Arabidopsis thaliana* were stained by propidium iodide, and the images were obtained by confocal microscope with the method of Seo et al. (2008) (FIGS. 5a and 5b).

Survival Rate Determination of Wild-Type and Transgenic *Arabidopsis thaliana* Plants after High Salt Stress 5-day-old wild type, 35S:CaSRP1 transgenic and each of knock-out plants, which had been grown under normal growth conditions, were subjected to high salt stress by growing in high salt-media containing 100 mM of NaCl for 7 days. Then, root lengths of each of plants were examined. As a result, each of the knock-out plants has a more sensitive phenotype to high salt stress compared with wild-type plants. Therefore, it could be demonstrated that AtSRPs act as a positive regulator in high salt stress response (FIG. 6).

Survival Rate Determination of Wild-Type and Transgenic *Arabidopsis thaliana* Plants after Drought Stress 3-week-old wild type, 35S:CaSRP1 transgenic and each of knock-out plants, which had been grown under normal growth conditions, were subjected to drought stress by withholding water for 8 days. The plants were then re-watered and their phenotypes were examined after 3 days. Survival was defined as the ability to resume growth when returned to normal conditions following water stress (Cho et al. 2008). Each of survival rates was as follows (FIG. 7a): wild type plants, 26.97% (24 out of 89 plants); 35S:AtSRP1 transgenic plants, 64.84% (59 out of 91 plants); 35S:AtSRP2 transgenic plants, 66.29% (59 out of 89 plants); 35S:AtSRP3 transgenic plants, 58.02% (47 out of 81 plants); atsrp1 mutant plants, 3.90% (3 out of 77 plants); atsrp3 mutant plants, 0.00% (0 out of 101 plants). In addition, transgenic plants showed significantly lower decreases of the moisture contents by the lapse of time, as compared to the wild-type and knock-out mutant plants (FIG. 7b).

Chlorophyll and Proline Content Measurements of Wild-Type and Transgenic *Arabidopsis thaliana* Plants after Drought Stress Chlorophyll was extracted in leaves of wild-type and AtSRPs-overexpressing transgenic *Arabidopsis thaliana* plants after drought stress by the method of Bae et al. (2009) using 80% acetone. The remaining leaf extract was dried at 105° C. for 16 hours, and weight of the dry extract was measured (Welti et al. 2002). Proline content of the leaves was measured by the method of Claussen (2005). As a result, transgenic plants exhibited significantly higher levels of proline contents, indicating that transgenic plants retained their leaf water more effectively than did wild-type leaves under drought conditions. In contrast, knock-out mutant plants showed opposite phenotypes (FIG. 8).

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

What is claimed is:

1. A method for improving a tolerance of a plant to drought stress or salt stress, comprising:
(a) introducing a nucleotide sequence encoding an amino acid sequence consisting of SEQ ID NO:6 to a cell of the plant; and
(b) obtaining a transgenic plant exhibiting improved tolerance to drought stress or salt stress from the cell of the plant.

2. The method according to claim 1, wherein the nucleotide sequence encoding the amino acid sequence of SEQ ID NO:6 comprises the nucleotide sequence as set forth in SEQ ID NO:3.

3. The method according to claim 1, wherein the nucleotide sequence comprises (i) the nucleotide sequence encoding the amino acid sequence of SEQ ID NO:6; (ii) a promoter operably linked to the nucleotide sequence of (i); and (iii) a poly A signal sequence operably linked to the nucleotide sequence of (i).

4. The method according to claim 3, wherein the promoter of (ii) is selected from the group consisting of cauliflower mosaic virus (CaMV)-35S promoter, SP6 promoter, T7 promoter, T3 promoter, PM promoter, figwort mosaic virus 35S promoter, sugarcane bacilliform virus promoter, commelina yellow mottle virus promoter, photo-inducible promoter of small subunit of ribulose-1,5-bis-phosphate carboxylase (ssRUBISCO), cytosolic triosphosphate isomerase (TPI) promoter in rice, *Arabidopsis* adenine phosphoribosyltransferase (APRT), and *Arabidopsis* octopine synthase promoter.

5. The method according to claim 3, wherein the poly A signal sequence of (iii) is selected from the group consisting of 3'-non-translated region of *Agrobacterium tumefaciens* nopaline synthase gene, 3'-non-translated region of *Agrobacterium tumefaciens* octopine synthase gene, 3'-end of potato protease inhibitor I gene, 3'-end of potato protease inhibitor II gene, 3'-end of tomato protease inhibitor I gene, 3'-end of tomato protease inhibitor II gene, and cauliflower mosaic virus (CaMV) 35S terminator.

6. A method for promoting a growth rate of a plant, comprising:
(a) introducing a nucleotide sequence encoding the amino acid sequence consisting of SEQ ID NO:6 to a cell of the plant; and
(b) obtaining a transgenic plant exhibiting improved tolerance to drought stress or salt stress from the cell of the plant.

7. The method according to claim 6, wherein the nucleotide sequence encoding the amino acid sequence of SEQ ID NO:6 comprises the nucleotide sequence as set forth in SEQ ID NO:3.

8. The method according to claim 6, wherein the nucleotide sequence comprises (i) the nucleotide sequence encoding the amino acid sequence of SEQ ID NO:6; (ii) a promoter operably linked to the nucleotide sequence of (i); and (iii) a poly A signal sequence operably linked to the nucleotide sequence of (i).

9. The method according to claim 8, wherein the promoter of (ii) is selected from the group consisting of cauliflower mosaic virus (CaMV)-35S promoter, SP6 promoter, T7 promoter, T3 promoter, PM promoter, figwort mosaic virus 35S promoter, sugarcane bacilliform virus promoter, commelina yellow mottle virus promoter, photo-inducible promoter of small subunit of ribulose-1,5-bis-phosphate carboxylase (ssRUBISCO), cytosolic triosphosphate isomerase (TPI) promoter in rice, *Arabidopsis* adenine phosphoribosyltransferase (APRT), and *Arabidopsis* octopine synthase promoter.

10. The method according to claim 8, wherein the poly A signal sequence of (iii) is selected from the group consisting of 3'-non-translated region of *Agrobacterium tumefaciens* nopaline synthase gene, 3'-non-translated region of *Agrobacterium tumefaciens* octopine synthase gene, 3'-end of potato protease inhibitor I gene, 3'-end of potato protease inhibitor II gene, 3'-end of tomato protease inhibitor I gene, 3'-end of tomato protease inhibitor II gene, and cauliflower mosaic virus (CaMV) 35S terminator.

* * * * *

SEQUENCE LISTING

```
<160> NUMBER OF SEQ ID NOS: 22

<210> SEQ ID NO 1
<211> LENGTH: 723
<212> TYPE: DNA
<213> ORGANISM: Arabidopsis thaliana

<400> SEQUENCE: 1
atggagacag agaagaaaaa tagcaaggag gtagcgctaa aacacctagc gttcgtgaga      60
attgcaacga tccatattct ggcttccgtc tcaaatctct acgaatacgc taaacaaaac     120
tccggtcctc tcaaatccgc cgtggaaaag gtcgaaggag ccgtcaccac cgtcgtcacc     180
cctgtctatc agaaattcaa agatgttcct gattctctcc tggtctttct agatcacaag     240
gtgggtgaag tttcgtacaa gtttgatgag catgctcctc caatggctaa gaaagtggtg     300
aatcaagcac atgtattgat ctacaaggcg acagagaaag ctcaaagctt tgtgaaagag     360
gctcgtaccg tggtcccaa agctgcgttt aactatgctg caactgagta caagtttttc      420
gttgtgacca actcggttaa agtctgggct aaacttaacc agtataaacc aatccatgca     480
atgggtgaca aagctttgcc tgtggctgca cacttttcca gtcggtacaa cgatttggtg     540
actgatatga ctaatatggg ttactctttg gttggttatc ttccgttggt tcctgttgat     600
gacattgtta aggcttatga aaaggaagat gcaaggagaa agaaaggagg ggatacggct     660
ggaaagaaag gagagactac tgatgcggct gatggtgata aatcatcgtc tgattcggag     720
tag                                                                    723

<210> SEQ ID NO 2
<211> LENGTH: 708
<212> TYPE: DNA
<213> ORGANISM: Arabidopsis thaliana

<400> SEQUENCE: 2
atggctgaag atgaaatagt agtcgaagaa gagcaatcac agccacagga gattactcca      60
gttccaccat cttcttcgtc ttcgccttcg ttagtggtgg aagacgacga tgagatgaag     120
ctcaagcact tggaattcat tcaagtcgcg gcggtttact tcgccgcctg tttctcgacc     180
ctctacgagt tggctaaaga caacgctggt ccactcaaac tcggcgtcga gaacattgaa     240
gattgcgttc gaaccgtgct tgctccatta tacgaaaaat tccacgacgt tcctttcaag     300
cttctccttt tcgtcgatcg taaggtggac gatgtgttct tcgatgttga gacatatgtt     360
ccgtcattgg tgaagcaagc ttctagccaa gcgctcacgg tggccacgga ggtgcagcgc     420
accggcgttg tggacactac caagagcatt gcaagaagcg tccgggacaa gtacgagcca     480
gcggcagagt attacgcagc gacgctgtgg cgtttactga tcaactgcc gttgttccct     540 gaagttgcgc atttagtgat ccccacggcg tttactggt cagagaagta caacgatgcg     600
gttcgttacg ttggcgacag agactacttt ggggcagagt atctacccat gattcctatt     660
gagaagatct ctgatatttt ggaacaagat cagtgtcgag ctgattga                 708

<210> SEQ ID NO 3
<211> LENGTH: 741
```

<212> TYPE: DNA
<213> ORGANISM: Arabidopsis thaliana

<400> SEQUENCE: 3

```
atggctactc aaacggatct cgctcagccc aagcttgata tgaccaagga ggagaaagag    60
aggttgaagt atttgcaatt cgtgcaagct gctgctgtgg aagctctgct tcgctttgct   120
cttatttacg ctaaggcaaa ggacaagtct ggtcctttga aacctggtgt tgaatctgtt   180
gaaggagctg tcaagactgt cgttggtcct gtctacgaga ataccacga cgtccctgtt   240
gaggtcctta atacatgga ccagaaggtt gatatgtctg tgactgagct tgaccgtcgt   300
gtcccaccag tcgtcaagca agtgtctgcc caagccatct ccgctgctca gatagcaccc   360
attgtggcac gtgcgttggc ctctgaggtt cgacgtgctg gtgttgttga accgcttct   420
ggaatggcta atccgtcta ctccaagtac gagcctgctg ctaaggagtt gtatgcaaac   480
tatgagccaa agcagagca gtgtgccgtt tcagcttgga agaagcttaa ccagcttcct   540
ctattcccaa gctggctca agttgctgta ccaacagctg ctttctgctc tgagaagtac   600
aatgatactg tggttaaggc tgcagagaaa gggtacagag tcacatcgta catgccattg   660
gttccaacag agaggatctc aaaaatcttc gctgaggaga agctgagac cgagcctttg   720
gagttccatc cacttgattg a                                             741
```

<210> SEQ ID NO 4
<211> LENGTH: 240
<212> TYPE: PRT
<213> ORGANISM: Arabidopsis thaliana

<400> SEQUENCE: 4

```
Met Glu Thr Glu Lys Lys Asn Ser Lys Glu Val Ala Leu Lys His Leu
1               5                   10                  15

Ala Phe Val Arg Ile Ala Thr Ile His Ile Leu Ala Ser Val Ser Asn
            20                  25                  30

Leu Tyr Glu Tyr Ala Lys Gln Asn Ser Gly Pro Leu Lys Ser Ala Val
        35                  40                  45

Glu Lys Val Glu Gly Ala Val Thr Thr Val Val Thr Pro Val Tyr Gln
    50                  55                  60

Lys Phe Lys Asp Val Pro Asp Ser Leu Leu Val Phe Leu Asp His Lys
65                  70                  75                  80

Val Gly Glu Val Ser Tyr Lys Phe Asp Glu His Ala Pro Pro Met Ala
                85                  90                  95

Lys Lys Val Val Asn Gln Ala His Val Leu Ile Tyr Lys Ala Thr Glu
            100                 105                 110

Lys Ala Gln Ser Phe Val Lys Glu Ala Arg Thr Gly Gly Pro Lys Ala
        115                 120                 125

Ala Phe Asn Tyr Ala Ala Thr Glu Tyr Lys Phe Phe Val Val Thr Asn
    130                 135                 140

Ser Val Lys Val Trp Ala Lys Leu Asn Gln Tyr Lys Pro Ile His Ala
145                 150                 155                 160

Met Gly Asp Lys Ala Leu Pro Val Ala Ala His Phe Ser Ser Arg Tyr
                165                 170                 175

Asn Asp Leu Val Thr Asp Met Thr Asn Met Gly Tyr Ser Leu Val Gly
            180                 185                 190

Tyr Leu Pro Leu Val Pro Val Asp Asp Ile Val Lys Ala Tyr Glu Lys
        195                 200                 205

Glu Asp Ala Arg Arg Lys Lys Gly Gly Asp Thr Ala Gly Lys Lys Gly
```

```
            210                 215                 220
Glu Thr Thr Asp Ala Ala Asp Gly Asp Lys Ser Ser Asp Ser Glu
225                 230                 235                 240

<210> SEQ ID NO 5
<211> LENGTH: 235
<212> TYPE: PRT
<213> ORGANISM: Arabidopsis thaliana

<400> SEQUENCE: 5

Met Ala Glu Asp Glu Ile Val Val Glu Glu Gln Ser Gln Pro Gln
1               5                   10                  15

Glu Ile Thr Pro Val Pro Pro Ser Ser Ser Ser Pro Ser Leu Val
                20                  25                  30

Val Glu Asp Asp Glu Met Lys Leu Lys His Leu Glu Phe Ile Gln
            35                  40                  45

Val Ala Ala Val Tyr Phe Ala Ala Cys Phe Ser Thr Leu Tyr Glu Leu
50                  55                  60

Ala Lys Asp Asn Ala Gly Pro Leu Lys Leu Gly Val Glu Asn Ile Glu
65                  70                  75                  80

Asp Cys Val Arg Thr Val Leu Ala Pro Leu Tyr Glu Lys Phe His Asp
                85                  90                  95

Val Pro Phe Lys Leu Leu Leu Phe Val Asp Arg Lys Val Asp Asp Val
                100                 105                 110

Phe Phe Asp Val Glu Thr Tyr Val Pro Ser Leu Val Lys Gln Ala Ser
            115                 120                 125

Ser Gln Ala Leu Thr Val Ala Thr Glu Val Gln Arg Thr Gly Val Val
            130                 135                 140

Asp Thr Thr Lys Ser Ile Ala Arg Ser Val Arg Asp Lys Tyr Glu Pro
145                 150                 155                 160

Ala Ala Glu Tyr Tyr Ala Ala Thr Leu Trp Arg Leu Leu Asn Gln Leu
                165                 170                 175

Pro Leu Phe Pro Glu Val Ala His Leu Val Ile Pro Thr Ala Phe Tyr
            180                 185                 190

Trp Ser Glu Lys Tyr Asn Asp Ala Val Arg Tyr Val Gly Asp Arg Asp
            195                 200                 205

Tyr Phe Gly Ala Glu Tyr Leu Pro Met Ile Pro Ile Glu Lys Ile Ser
210                 215                 220

Asp Ile Leu Glu Gln Asp Gln Cys Arg Ala Asp
225                 230                 235

<210> SEQ ID NO 6
<211> LENGTH: 246
<212> TYPE: PRT
<213> ORGANISM: Arabidopsis thaliana

<400> SEQUENCE: 6

Met Ala Thr Gln Thr Asp Leu Ala Gln Pro Lys Leu Asp Met Thr Lys
1               5                   10                  15

Glu Glu Lys Glu Arg Leu Lys Tyr Leu Gln Phe Val Gln Ala Ala
                20                  25                  30

Val Glu Ala Leu Leu Arg Phe Ala Leu Ile Tyr Ala Lys Ala Lys Asp
            35                  40                  45

Lys Ser Gly Pro Leu Lys Pro Gly Val Glu Ser Val Glu Gly Ala Val
            50                  55                  60

Lys Thr Val Val Gly Pro Val Tyr Glu Lys Tyr His Asp Val Pro Val
```

```
                65                  70                  75                  80
Glu Val Leu Lys Tyr Met Asp Gln Lys Val Asp Met Ser Val Thr Glu
                    85                  90                  95

Leu Asp Arg Arg Val Pro Pro Val Val Lys Gln Val Ser Ala Gln Ala
                100                 105                 110

Ile Ser Ala Ala Gln Ile Ala Pro Ile Val Ala Arg Ala Leu Ala Ser
                115                 120                 125

Glu Val Arg Arg Ala Gly Val Val Glu Thr Ala Ser Gly Met Ala Lys
                130                 135                 140

Ser Val Tyr Ser Lys Tyr Glu Pro Ala Ala Lys Glu Leu Tyr Ala Asn
145                 150                 155                 160

Tyr Glu Pro Lys Ala Glu Gln Cys Ala Val Ser Ala Trp Lys Lys Leu
                165                 170                 175

Asn Gln Leu Pro Leu Phe Pro Arg Leu Ala Gln Val Ala Val Pro Thr
                180                 185                 190

Ala Ala Phe Cys Ser Glu Lys Tyr Asn Asp Thr Val Val Lys Ala Ala
                195                 200                 205

Glu Lys Gly Tyr Arg Val Thr Ser Tyr Met Pro Leu Val Pro Thr Glu
                210                 215                 220

Arg Ile Ser Lys Ile Phe Ala Glu Glu Lys Ala Glu Thr Glu Pro Leu
225                 230                 235                 240

Glu Phe His Pro Leu Asp
                245

<210> SEQ ID NO 7
<211> LENGTH: 31
<212> TYPE: DNA
<213> ORGANISM: Artificial Sequence
<220> FEATURE:
<223> OTHER INFORMATION: forward primer for Cloning of AtSRPs ORF,
      RT-PCR and preparation of transgenic plant

<400> SEQUENCE: 7
gcggatccat ggagacagag aagaaaaata g                                         31

<210> SEQ ID NO 8
<211> LENGTH: 28
<212> TYPE: DNA
<213> ORGANISM: Artificial Sequence
<220> FEATURE:
<223> OTHER INFORMATION: reverse primer for Cloning of AtSRPs ORF,
      RT-PCR and preparation of transgenic plant

<400> SEQUENCE: 8
gcgagctcct actccgaatc agacgatg                                             28

<210> SEQ ID NO 9
<211> LENGTH: 32
<212> TYPE: DNA
<213> ORGANISM: Artificial Sequence
<220> FEATURE:
<223> OTHER INFORMATION: forward primer for Cloning of AtSRPs ORF,
      RT-PCR and preparation of transgenic plant

<400> SEQUENCE: 9
gcggatccat ggctgaagat gaaatagtag tc                                        32

<210> SEQ ID NO 10
<211> LENGTH: 29
<212> TYPE: DNA
<213> ORGANISM: Artificial Sequence
```

```
<220> FEATURE:
<223> OTHER INFORMATION: reverse primer for Cloning of AtSRPs ORF,
      RT-PCR and preparation of transgenic plant

<400> SEQUENCE: 10
gcgagctctc aatcagctcg acactgatc                                            29

<210> SEQ ID NO 11
<211> LENGTH: 29
<212> TYPE: DNA
<213> ORGANISM: Artificial Sequence
<220> FEATURE:
<223> OTHER INFORMATION: forward primer for Cloning of AtSRPs ORF,
      RT-PCR and preparation of transgenic plant

<400> SEQUENCE: 11
gcggatccat ggctactcaa acggatctc                                            29

<210> SEQ ID NO 12
<211> LENGTH: 29
<212> TYPE: DNA
<213> ORGANISM: Artificial Sequence
<220> FEATURE:
<223> OTHER INFORMATION: reverse primer for Cloning of AtSRPs ORF,
      RT-PCR and preparation of transgenic plant

<400> SEQUENCE: 12
gcgagctctc aatcaagtgg atggaactc                                            29

<210> SEQ ID NO 13
<211> LENGTH: 20
<212> TYPE: DNA
<213> ORGANISM: Artificial Sequence
<220> FEATURE:
<223> OTHER INFORMATION: forward primer for Cloning of AtSRPs ORF,
      RT-PCR and preparation of transgenic plant

<400> SEQUENCE: 13
gcatttgcca aggatgtttt                                                      20

<210> SEQ ID NO 14
<211> LENGTH: 20
<212> TYPE: DNA
<213> ORGANISM: Artificial Sequence
<220> FEATURE:
<223> OTHER INFORMATION: reverse primer for Cloning of AtSRPs ORF,
      RT-PCR and preparation of transgenic plant

<400> SEQUENCE: 14
gtacaaaggg cagggacgta                                                      20

<210> SEQ ID NO 15
<211> LENGTH: 27
<212> TYPE: DNA
<213> ORGANISM: Artificial Sequence
<220> FEATURE:
<223> OTHER INFORMATION: forward primer for Cloning of AtSRPs ORF,
      RT-PCR and preparation of transgenic plant

<400> SEQUENCE: 15
tactgattac ctcatgaaga tccttac                                              27

<210> SEQ ID NO 16
<211> LENGTH: 26
<212> TYPE: DNA
<213> ORGANISM: Artificial Sequence
<220> FEATURE:
```

```
<223> OTHER INFORMATION: reverse primer for Cloning of AtSRPs ORF,
      RT-PCR and preparation of transgenic plant

<400> SEQUENCE: 16
aaacgatgtc tctttagttt agaagc                                          26

<210> SEQ ID NO 17
<211> LENGTH: 20
<212> TYPE: DNA
<213> ORGANISM: Artificial Sequence
<220> FEATURE:
<223> OTHER INFORMATION: Quantitative real time RT-PCR forward primer

<400> SEQUENCE: 17
tgattctctc ctggtctttc                                                 20

<210> SEQ ID NO 18
<211> LENGTH: 20
<212> TYPE: DNA
<213> ORGANISM: Artificial Sequence
<220> FEATURE:
<223> OTHER INFORMATION: Quantitative real time RT-PCR reverse primer

<400> SEQUENCE: 18
ttctctgtcg ccttgtagat                                                 20

<210> SEQ ID NO 19
<211> LENGTH: 18
<212> TYPE: DNA
<213> ORGANISM: Artificial Sequence
<220> FEATURE:
<223> OTHER INFORMATION: Quantitative real time RT-PCR forward primer

<400> SEQUENCE: 19
ttttcgtcga tcgtaagg                                                   18

<210> SEQ ID NO 20
<211> LENGTH: 20
<212> TYPE: DNA
<213> ORGANISM: Artificial Sequence
<220> FEATURE:
<223> OTHER INFORMATION: Quantitative real time RT-PCR reverse primer

<400> SEQUENCE: 20
aatgctcttg gtagtgtcca                                                 20

<210> SEQ ID NO 21
<211> LENGTH: 20
<212> TYPE: DNA
<213> ORGANISM: Artificial Sequence
<220> FEATURE:
<223> OTHER INFORMATION: Quantitative real time RT-PCR forward primer

<400> SEQUENCE: 21
ccctgttgag gtccttaaat                                                 20

<210> SEQ ID NO 22
<211> LENGTH: 17
<212> TYPE: DNA
<213> ORGANISM: Artificial Sequence
<220> FEATURE:
<223> OTHER INFORMATION: Quantitative real time RT-PCR reverse primer

<400> SEQUENCE: 22
gccacaatgg gtgctat                                                    17
```